（12） United States Patent
Kenyon et al.

(10) Patent No.: US 10,588,567 B2
(45) Date of Patent: *Mar. 17, 2020

(54) ALERTNESS PREDICTION SYSTEM AND METHOD

(71) Applicant: CURAEGIS TECHNOLOGIES, INC., Rochester, NY (US)

(72) Inventors: Matt Kenyon, West Henrietta, NY (US); Colin Payne-Rogers, Rochester, NY (US); Josh Jones, West Henrietta, NY (US)

(73) Assignee: Curaegis Technologies, Inc., Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/364,003

(22) Filed: Mar. 25, 2019

(65) Prior Publication Data

US 2019/0216391 A1 Jul. 18, 2019

Related U.S. Application Data

(63) Continuation of application No. 15/436,039, filed on Feb. 17, 2017, now Pat. No. 10,238,335.

(Continued)

(51) Int. Cl.
*A61B 5/01* (2006.01)
*A61B 5/00* (2006.01)
(Continued)

(52) U.S. Cl.
CPC .......... *A61B 5/4857* (2013.01); *A61B 5/0022* (2013.01); *A61B 5/01* (2013.01);
(Continued)

(58) Field of Classification Search
CPC ................................ A61B 5/4857; A61B 5/01
See application file for complete search history.

(56) References Cited

U.S. PATENT DOCUMENTS 509,791 A 11/1893 Callender
600,806 A 3/1898 Scott
(Continued)

FOREIGN PATENT DOCUMENTS

CN 202443558 U 9/2012
CN 102881117 A 1/2013
(Continued)

OTHER PUBLICATIONS

International Search Report dated Nov. 24, 2015 for International Application No. PCT/US2015/048881.
(Continued)

*Primary Examiner* — Qutbuddin Ghulamali
(74) *Attorney, Agent, or Firm* — Dinsmore & Shohl LLP

(57) ABSTRACT

An alertness prediction bio-mathematical model for use in devices such as a wearable device that improves upon previous models of predicting fatigue and alertness by gathering data from the individual being monitored to create a more accurate estimation of alertness levels. The bio-mathematical model may be a two-process algorithm which incorporates a sleep-wake homeostasis aspect and a circadian rhythm aspect. The sleep-wake homeostasis aspect of the model is improved by using actigraphy measures in conjunction with distal skin, ambient light and heart rate measures to improve the accuracy of the sleep and wake estimations. The circadian rhythm model aspect improves fatigue prediction and estimation by using distal skin, heart rate and actigraphy data. The sleep-wake homeostasis and circadian rhythm aspects may also be combined with additional objective and subjective measures as well as information from a user to improve the accuracy of the alertness estimation even further.

1 Claim, 9 Drawing Sheets

Related U.S. Application Data

(60) Provisional application No. 62/432,977, filed on Dec. 12, 2016, provisional application No. 62/296,800, filed on Feb. 18, 2016.

(51) Int. Cl.

| | | |
|---|---|---|
| *A61B 5/0205* | (2006.01) | |
| *A61B 5/11* | (2006.01) | |
| *A61B 5/16* | (2006.01) | |
| *G16H 50/50* | (2018.01) | |
| *G16H 50/30* | (2018.01) | |
| *G16H 50/20* | (2018.01) | |
| *A61B 5/18* | (2006.01) | |
| *G16H 20/00* | (2018.01) | |
| *A61B 5/024* | (2006.01) | |

(52) U.S. Cl.
CPC ........ *A61B 5/0205* (2013.01); *A61B 5/02055* (2013.01); *A61B 5/11* (2013.01); *A61B 5/165* (2013.01); *A61B 5/18* (2013.01); *A61B 5/4809* (2013.01); *A61B 5/7267* (2013.01); *A61B 5/7275* (2013.01); *A61B 5/7278* (2013.01); *A61B 5/7282* (2013.01); *G16H 20/00* (2018.01); *G16H 50/20* (2018.01); *G16H 50/30* (2018.01); *G16H 50/50* (2018.01); *A61B 5/02438* (2013.01); *A61B 5/1118* (2013.01); *A61B 2560/0242* (2013.01)

(56) References Cited

U.S. PATENT DOCUMENTS

| | | |
|---|---|---|
| 2,875,430 A | 2/1959 | Kayser, Jr. |
| 3,186,508 A | 6/1965 | Lamont |
| 3,222,639 A | 12/1965 | Kayser, Jr. |
| 3,222,640 A | 12/1965 | Wurst |
| 3,223,998 A | 12/1965 | Hose |
| 3,524,030 A | 8/1970 | Wiegel |
| 3,631,446 A | 12/1971 | Setser |
| 3,654,599 A | 4/1972 | Sepper |
| 3,861,349 A | 1/1975 | Conley |
| 3,935,830 A | 2/1976 | Cox |
| 3,972,038 A | 7/1976 | Fletcher et al. |
| 3,980,999 A | 9/1976 | Nishioka |
| 4,007,357 A | 2/1977 | Yanagishima |
| 4,017,843 A | 4/1977 | Yanagishima |
| 4,059,830 A | 11/1977 | Threadgill |
| 4,104,621 A | 8/1978 | Yanagishima |
| 4,354,179 A | 10/1982 | Fourcade |
| 4,359,725 A | 11/1982 | Balogh et al. |
| 4,361,834 A | 11/1982 | King |
| 4,365,637 A | 12/1982 | Johnson et al. |
| 4,450,438 A | 5/1984 | Seko et al. |
| 4,463,347 A | 7/1984 | Seko et al. |
| 4,496,938 A | 1/1985 | Seko et al. |
| 4,509,531 A | 4/1985 | Ward |
| 4,518,954 A | 5/1985 | Seko et al. |
| 4,519,040 A | 5/1985 | Brankamp et al. |
| 4,564,833 A | 1/1986 | Seko |
| 4,564,993 A | 1/1986 | Blaurock et al. |
| 4,581,617 A | 4/1986 | Yoshimoto et al. |
| 4,586,032 A | 4/1986 | Seko et al. |
| 4,586,827 A | 5/1986 | Hirsch et al. |
| 4,594,583 A | 6/1986 | Seko et al. |
| 4,604,617 A | 8/1986 | Morozumi |
| 4,611,199 A | 9/1986 | Seko et al. |
| 4,673,913 A | 6/1987 | Akita et al. |
| 4,706,072 A | 11/1987 | Ikeyama |
| 4,794,536 A | 12/1988 | Eto et al. |
| 4,819,860 A | 4/1989 | Hargrove et al. |
| 4,853,672 A | 8/1989 | Yasuda et al. |
| 4,928,090 A | 5/1990 | Yoshimi et al. |
| 4,984,646 A | 1/1991 | Sano et al. |
| 4,996,647 A | 2/1991 | Gasser |
| 5,057,834 A | 10/1991 | Nordstrom |
| 5,259,390 A | 11/1993 | MacLean |
| 5,282,135 A | 1/1994 | Sato et al. |
| 5,311,877 A | 5/1994 | Kishi |
| 5,402,109 A | 3/1995 | Mannik |
| 5,465,079 A | 11/1995 | Bouchard et al. |
| 5,488,353 A | 1/1996 | Kawakami et al. |
| 5,497,779 A | 3/1996 | Takaya et al. |
| 5,515,858 A | 5/1996 | Myllymaki |
| 5,548,773 A | 8/1996 | Kemeny et al. |
| 5,568,127 A | 10/1996 | Bang |
| 5,570,087 A | 10/1996 | Lemelson |
| 5,570,698 A | 11/1996 | Liang et al. |
| 5,585,785 A | 12/1996 | Gwin et al. |
| 5,670,944 A | 9/1997 | Myllymaeki |
| 5,684,455 A | 11/1997 | Williams et al. |
| 5,684,462 A | 11/1997 | Gold |
| 5,689,241 A | 11/1997 | Clarke et al. |
| 5,694,116 A | 12/1997 | Kojima |
| 5,709,281 A | 1/1998 | Sherwin et al. |
| 5,714,925 A | 2/1998 | Lee et al. |
| 5,717,606 A | 2/1998 | Hara et al. |
| 5,729,619 A | 3/1998 | Puma |
| 5,745,031 A | 4/1998 | Yamamoto |
| 5,765,116 A | 6/1998 | Wilson et al. |
| 5,786,765 A | 7/1998 | Kumakura et al. |
| 5,795,306 A | 8/1998 | Shimotani et al. |
| 5,798,695 A | 8/1998 | Metalis et al. |
| 5,805,079 A | 9/1998 | Lemelson et al. |
| 5,805,720 A | 9/1998 | Suenaga et al. |
| 5,813,989 A | 9/1998 | Saitoh et al. |
| 5,813,993 A | 9/1998 | Kaplan et al. |
| 5,815,070 A | 9/1998 | Yoshikawa et al. |
| 5,821,860 A | 10/1998 | Yokoyama et al. |
| 5,835,008 A | 11/1998 | Colemere |
| 5,835,028 A | 11/1998 | Bender et al. |
| 5,847,648 A | 12/1998 | Savor et al. |
| 5,850,193 A | 12/1998 | Shimoura et al. |
| 5,867,587 A | 2/1999 | Aboutalib et al. |
| 5,900,819 A | 5/1999 | Kyrtsos |
| 5,907,282 A | 5/1999 | Tuorto et al. |
| 5,917,415 A | 6/1999 | Atlas |
| 5,923,263 A | 7/1999 | Rodriguez |
| 5,925,082 A | 7/1999 | Shimizu et al. |
| 5,939,989 A | 8/1999 | Bang |
| 5,942,979 A | 8/1999 | Luppino |
| 5,969,616 A | 10/1999 | Tschoi et al. |
| 5,982,287 A | 11/1999 | Brannen et al. |
| 5,990,795 A | 11/1999 | Miller |
| 6,023,227 A | 2/2000 | Yanko et al. |
| 6,061,610 A | 5/2000 | Boer |
| 6,064,301 A | 5/2000 | Takahashi et al. |
| 6,067,020 A | 5/2000 | Wimmer et al. |
| 6,087,641 A | 7/2000 | Kinouchi et al. |
| 6,087,943 A | 7/2000 | Bailey |
| 6,091,334 A | 7/2000 | Galiana et al. |
| 6,097,286 A | 8/2000 | Discenzo |
| 6,097,295 A | 8/2000 | Griesinger et al. |
| 6,172,610 B1 | 1/2001 | Prus |
| 6,184,791 B1 | 2/2001 | Baugh |
| 6,195,165 B1 | 2/2001 | Sayegh |
| 6,265,978 B1 | 7/2001 | Atlas |
| 6,313,749 B1 | 11/2001 | Horne et al. |
| 6,353,396 B1 | 3/2002 | Atlas |
| 6,545,607 B2 | 4/2003 | Bredow et al. |
| 6,686,845 B2 | 2/2004 | Oyama |
| 6,756,903 B2 | 6/2004 | Omry et al. |
| 6,762,684 B1 | 7/2004 | Camhi |
| 6,791,462 B2 | 9/2004 | Choi |
| 6,822,573 B2 | 11/2004 | Basir et al. |
| 6,950,027 B2 | 9/2005 | Banas |
| 7,019,623 B2 | 3/2006 | Klausner et al. |
| 7,084,773 B2 | 8/2006 | Oyama |
| 7,602,278 B2 | 10/2009 | Prost-Fin et al. |
| 7,605,694 B2 | 10/2009 | Prost-Fin et al. |
| 7,692,552 B2 | 4/2010 | Harrington et al. |
| 7,830,265 B2 | 11/2010 | Power |
| 7,839,292 B2 | 11/2010 | Wang et al. |
| 7,898,426 B2 | 3/2011 | Rai et al. |

(56) References Cited

U.S. PATENT DOCUMENTS

| | | | |
|---|---|---|---|
| 7,956,757 B2 | 6/2011 | Kumar et al. | |
| 8,033,916 B2 | 10/2011 | Caldwell et al. | |
| 8,123,624 B2 | 2/2012 | Caldwell | |
| 8,188,870 B2 | 5/2012 | Kumar et al. | |
| 8,199,018 B2 | 6/2012 | Shigetou | |
| 8,303,172 B2 | 11/2012 | Zei et al. | |
| 8,339,268 B2 | 12/2012 | Deng et al. | |
| 8,356,899 B2 | 1/2013 | Hirata | |
| 8,439,686 B2 | 5/2013 | Zayfert et al. | |
| 8,491,397 B2 | 7/2013 | Caldwell et al. | |
| 8,604,932 B2 | 12/2013 | Breed et al. | |
| 8,698,635 B2 | 4/2014 | Sullivan et al. | |
| 8,725,311 B1 | 5/2014 | Breed | |
| 8,742,936 B2 | 6/2014 | Galley et al. | |
| 8,773,269 B2 | 7/2014 | Richardson et al. | |
| 8,812,428 B2 * | 8/2014 | Mollicone | G06N 5/048 706/52 |
| 8,823,527 B2 | 9/2014 | Husen et al. | |
| 2004/0044293 A1 | 3/2004 | Burton | |
| 2004/0145493 A1 | 7/2004 | O'Connor et al. | |
| 2005/0070824 A1 | 3/2005 | Rhad et al. | |
| 2006/0282021 A1 | 12/2006 | DeVaul et al. | |
| 2007/0167850 A1 | 7/2007 | Russell et al. | |
| 2008/0174451 A1 | 7/2008 | Harrington et al. | |
| 2008/0180235 A1 | 7/2008 | Chang | |
| 2008/0266118 A1 | 10/2008 | Pierson et al. | |
| 2009/0189772 A1 | 7/2009 | Christ et al. | |
| 2009/0268022 A1 | 10/2009 | Omi | |
| 2009/0273478 A1 | 11/2009 | Mei | |
| 2010/0100004 A1 * | 4/2010 | van Someren | A61B 5/0008 600/549 |
| 2010/0137748 A1 | 6/2010 | Sone et al. | |
| 2010/0138379 A1 * | 6/2010 | Mott | A61B 5/4857 706/52 |
| 2011/0077548 A1 | 3/2011 | Torch | |
| 2011/0080285 A1 | 4/2011 | Howson et al. | |
| 2011/0175726 A1 | 7/2011 | Baird et al. | |
| 2012/0007735 A1 | 1/2012 | Rhyins | |
| 2012/0316456 A1 | 12/2012 | Rahman et al. | |
| 2013/0018284 A1 | 1/2013 | Kahn et al. | |
| 2013/0120106 A1 | 5/2013 | Cauwels et al. | |
| 2014/0077957 A1 | 3/2014 | Bichara | |
| 2014/0081179 A1 | 3/2014 | Moore-Ede | |
| 2014/0085077 A1 | 3/2014 | Luna et al. | |
| 2014/0253325 A1 | 9/2014 | Ky | |
| 2015/0109124 A1 * | 4/2015 | He | A61B 5/0285 340/539.12 |
| 2015/0186594 A1 * | 7/2015 | Zhang | A61N 5/0618 703/2 |
| 2015/0223743 A1 * | 8/2015 | Pathangay | A61B 5/18 600/301 |
| 2015/0313529 A1 * | 11/2015 | Nevo | A61B 5/165 600/595 |

FOREIGN PATENT DOCUMENTS

| | | |
|---|---|---|
| CN | 202929361 U | 5/2013 |
| CN | 203552404 U | 4/2014 |
| CN | 102881117 B | 11/2014 |
| DE | 10041116 A1 | 7/2001 |
| EP | 793582 A1 | 9/1997 |
| EP | 853559 A4 | 7/2000 |
| EP | 853559 A1 | 3/2002 |
| EP | 853559 B1 | 3/2002 |
| GB | 2334127 A | 8/1999 |
| GB | 2375645 A | 11/2002 |
| GB | 2375645 A8 | 3/2004 |
| WO | 200854460 A2 | 5/2008 |
| WO | 2008054460 A3 | 6/2008 |
| WO | 2012144948 A1 | 10/2012 |
| WO | 2016019002 A1 | 2/2016 |

OTHER PUBLICATIONS

International Preliminary Report and Written Opinion dated dated Mar. 23, 2017 for International Application No. PCT/US2015/048881.

2014 Bluetooth Watch New Wearable Electronic Device L12 Wristband NFC Handsfree Car Kit Wireless Smart Watch for iPhone, Nov. 13, 2014, pp. 1-6, retrieved from http://smartfly.en.alibaba.com/Handsfree_Car_Kit_Wireless_Smart_Watch_for_iphone.html.

Brunel University London, Brunel Students Design Set to Reduce Number of Crashes on our Roads, Press Release May 25, 2006, p. 1, retrieved from http://www.brunel.ac.uk/news-and-events/news/news-items/press/ne_24830.

Caterppillar, Operator Fatigue Detection Technology Review, 2008, pp. 1-5, retrieved from https://safety.cat.com/cda/files/771871/7/fatigue_report_021108.pdf.

Cinaz, B. et al., A Wearable User Interface for Measuring Reaction Time, Ambient Intelligence, 2011, pp. 1-10.

Fatigue Science, The Readiband System, Nov. 13, 2014, pp. 1-3, retrieved from http://fatiguescience.com/solutions/readiband/.

Fitness Wristbands Manufacturer, Fitness Wristbands with Pedometer/Sleep Monitor Calorie counter/Waterproof Function, Nov. 13, 2014, pp. 1-3, retrieved from http://www.globalsources.com/gsol/l/Smart-bracelet/p/sm/1107796260.htm#1107796260.

Horsey, Julian, Geeky Gadgets, Stay Awake and Focused During the Day Using the Spark Watch, Jul. 7, 2014, pp. 1-4, retrieved from http://www.geeky-gadgets.com/stay-awake-and-focused-during-the-day-using-the-spark-watch-07-07-2014/.

Huayang, HuaYang Fashion Movement Monitoring Tracking Fatigue Remind 4.0 Bluetooth Bracelet Wristband, Jul. 8, 2014, p. 1-3, retrieved from http://www.amazon.co.uk/HuaYang-Movement-Monitoring-Bluetooth-Wristband/dp/B00LLV2Q7M.

Ivorra, A. et al., Minimally Obtrusive Wearable Device for Continuous Interactive Cognitive and Neurological Assessment, Physiol MEas, 2008, pp. 1-14.

Neurontools, Attention Meter, Nov. 13, 2014, pp. 1-2, retrieved from http://www.neurontools.com/attention_meter.html.

Pedley, Mark, Tilt Sensing Using a Three-Axis Accelerometer, Freescale Semiconductor, Document No. AN3461, Revision 6, Mar. 2013, pp. 1-22.

RIDEROOM, Driver-Fatigue Bracelet, May 16, 206, pp. 1-2, retrieved from http://www.rideroom.com/news_comments.php?id-2389.

ISR/WO issued in corresponding PCT Application No. PCT/US2017/018355, dated May 15, 2017 (May 15, 2017).

International Preliminary Report on Patentability pertaining to PCT/US2017/018355 dated Aug. 21, 2018.

\* cited by examiner

ALERTNESS PREDICTION SYSTEM AND METHOD

CROSS-REFERENCE TO RELATED APPLICATION(S)

This application is a Continuation application of U.S. patent application Ser. No. 15/436,039, filed Feb. 17, 2017 entitled Alertness Prediction System and Method, which claims priority to U.S. Provisional application Ser. No. 62/296,800 entitled Alertness Prediction Algorithm, filed on Feb. 18, 2016 and U.S. Provisional application Ser. No. 62/432,977 entitled Alertness Prediction System and Method, filed on Dec. 12, 2016, the contents of each incorporated fully herein by reference.

BACKGROUND OF THE INVENTION

The unchecked degradation of an individual's alertness is a growing concern and the consequences in some areas are approaching epidemic proportions. As an example, it is estimated that 250,000 drivers per day fall asleep at the wheel. Serious and fatal truck, bus, train and automobile accidents are occurring at an alarming rate. Many injuries and accidents in manufacturing plants are fatigue related. The purpose of monitoring alertness is to prevent these and other emergency situations from happening rather than dealing with them after the fact. For instance, it is already too late to wake someone up after they have fallen asleep at the wheel.

Historically, algorithms for predicting or estimating an individual's alertness were based upon what is often referred to as a two process model. The two process model is made up of a circadian rhythm process and a sleep-wake homeostasis model. The circadian rhythm aspect of the model is typically based solely on a standard time period (e.g., 23-25 hours). The sleep-wake homeostasis model, on the other hand, is typically based solely on actigraphy determinations.

A weakness to the current form of the two process algorithmic model is that it generalizes its prediction of alertness based upon data gathered from a small sample set. In general, the algorithm suffers from a lack of personalization to the individual for which it is intended to be used.

SUMMARY OF THE INVENTION

Aspects of the invention aim to improve upon previous models of predicting fatigue and alertness levels by gathering data from the individual being monitored to create a more accurate estimation of the individual's alertness levels. An algorithm or bio-mathematical model may be incorporated into a wearable device to detect, predict and/or estimate an individual's alertness based upon a culmination of subjective and objective measures.

One algorithmic bio-mathematical model in accordance with an aspect of the invention involves a two-process algorithm incorporating a sleep-wake homeostasis determination and a circadian rhythm estimation. The sleep-wake homeostasis aspect of the model may be improved by using actigraphy measures, in addition to distal skin, ambient light, and heart rate measures, to improve the accuracy of the sleep and wake determinations for the individual. The circadian rhythm model of fatigue prediction and estimation may be improved by combining distal skin, heart rate and actigraphy data. This circadian rhythm estimate produces a more accurate model that is able to capture a user's mid-afternoon lull and evening increase in alertness levels. The sleep-wake homeostasis and circadian rhythm models may also be combined with additional objective and subjective measures as well as information supplied by the user to improve the accuracy of the estimation even further.

Other bio-mathematical models in accordance with aspects of the invention may generate fatigue scores that predict the alertness of an individual using various metrics. The bio-mathematical models, and devices, systems, and methods incorporating the bio-mathematical models described herein, could be used in scenarios where the alertness of an individual is of interest. The bio-mathematical model can reside on a stand-alone device (such as a wearable device) as an application or within another software environment. Some, or all, of the metrics of interest could be gathered and fed through the bio-mathematical model to produce an output that is correlated to an individual's alertness level.

Existing systems and algorithmic models that estimate or predict an individual's alertness level may be trained to a sample set of individuals and contain little to no feedback for circadian rhythm estimation. This produces highly inaccurate models of an individual's actual circadian rhythm and often misses predictions of known circadian events (such as the mid-afternoon lull and evening wakefulness) due to the generalized and simple sinusoids. The inventive devices, systems, and bio-mathematical models described herein, however, continue to improve their accuracy as the models adapt to the individual's circadian rhythm. The proposed models may be personalized to an individual where other systems are generalized to a sample set of data.

BRIEF DESCRIPTION OF THE DRAWINGS

The invention is best understood from the following detailed description when read in connection with the accompanying drawings, with like elements having the same reference numerals. When a plurality of similar elements are present, a single reference numeral may be assigned to the plurality of similar elements with a small letter designation referring to specific elements. When referring to the elements collectively or to a non-specific one or more of the elements, the small letter designation may be dropped. This emphasizes that according to common practice, the various features of the drawings are not drawn to scale. On the contrary, the dimensions of the various features are arbitrarily expanded or reduced for clarity. Included in the drawings are the following figures.

DETAILED DESCRIPTION OF THE INVENTION

Aspects of the invention provide a wearable device having a bio-mathematical model which predicts fatigue levels for an individual using various metrics. Certain aspects involve a two-process algorithm, a type of bio-mathematical model, which predicts alertness levels by using accurate measures of actigraphy and estimations of an individual's circadian rhythm. The wearable device may also be connected to or in communication with other systems such as, for example, a smart phone application or other "smart" devices. Both actigraphy and circadian rhythm estimations can be made using measurements of the individual's movement, body position, heart rate, and distal skin temperature. The alertness prediction of the bio-mathematical model can be further improved in accuracy by including additional objective and subjective measures, which are described in further detail herein. The bio-mathematical model enables improvements due to closed loop feedback and through continuous learning and monitoring.

Figure 1:
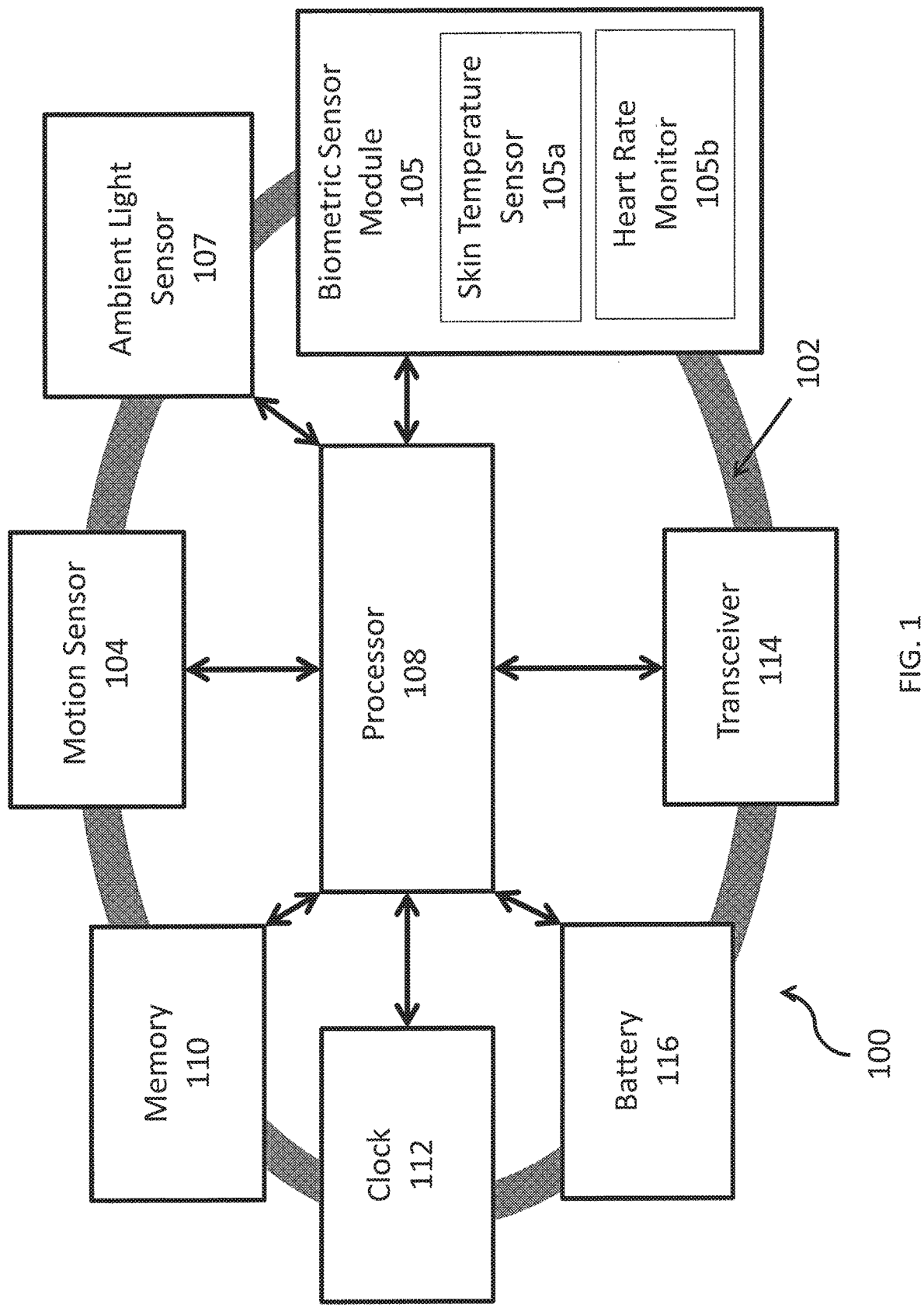
FIG. 1 is a block diagram of a wearable device in accordance with aspects of the present invention.

FIG. 1 depicts a wearable device 100 for monitoring an individual's fatigue and providing a prediction of the individual's alertness levels, e.g., to the individual wearing the device 100 and/or another entity. A suitable wearable device is described in U.S. Utility application Ser. No. 14/848,771. The illustrated wearable device 100 is embodied in a band 102, which may be placed on the individual's wrist, for example. The band 102 supports at least one motion sensor 104 and at least one biometric sensor module 105 for monitoring the individual's biometrics. The biometric sensor module 105 may include at least one of a skin temperature sensor 105*a* or a heart rate monitor 105*b*. Suitable motion sensors 104 and biometric sensor modules 105 for use with the present invention will be understood by one of skill in the art from the description herein.

The motion sensor 104 may include one or more gyroscopes and/or accelerometers to track movements (linear, angular, etc.). The movements monitored or tracked may include prescribed motions of the user, other movements by the user outside of prescribed motions, the user's relative motion, or motion caused by the user's environment (such as vibration from a truck engine, etc.). In addition to measuring movement, the motion sensor 104 may be used to estimate the user's body position (e.g. sitting, standing, lying down).

Techniques for tracking movements and/or body position are through accelerometers and/or gyroscopes. There are many small, low-power gyroscopes available on the market. The gyroscopes typically employ piezoelectric sensors or other forms of micro-electronic motion sensors (MEMS). For instance, SGS-Thompson Microelectronics (st.com) has a line of MEMS based gyroscopes that operate on low power, measure all three axes of movement, provide digital output that can be fed directly into a microprocessor, and that have a low noise threshold and low gyroscopic drift, allowing them to measure the fine movements with high precision and repeatability. The L3G3200D is a suitable device having an operational voltage range from 2.4V to 3.5V, which is well suited for battery operation, consumes only 6.1 mA in typical operation, has an operating range of −40 to +85 degrees Celsius, includes an embedded temperature sensor, and has digital output of both temperature and angular rates of movement, with up to 16-bits of precision for angular rates.

As an alternative to a MEMS gyroscopes, linear accelerometers may be used. Since MEMS linear accelerometers respond to the gravitational field as well as linear acceleration, when arranged in a three-axis configuration, it is possible to compute rotational changes to yaw, pitch, and roll, as described in the paper "Tilt Sensing Using a Three-Axis Accelerometer," by Mark Pedley; Freescale Semiconductor, Document Number AN3461, Revision 6, March 2013, which is incorporated fully herein by reference.

The biometric sensor module 105 may include one or more sensors to measure one or more biomarkers of the user. Biomarkers that may be measured in accordance with aspects of this invention include, but are not limited to, skin temperature and heart-related metrics, including heart rate. The biometric sensor module 105 may be used for continual and/or periodic passive measurements of various biomarkers of a user, e.g., at a rate of one measurement per minute. In some embodiments, the biometric sensor module 105 may be generic and may include both biometric sensors and non-biometric sensors (e.g., an ambient light sensor 107). In an embodiment, the biometric sensor module 105 may be integrated as a unit within the device 100. In another embodiment, the biometric sensor module 105 may be comprised of several components dispersed within and/or throughout the device 100.

The biometric sensor module 105 may include a skin temperature sensor 105*a* and a heart rate sensor 105*b*, such as the Pulse Rate Sensor from Karlsson Robotics. The skin temperature sensor 105*a* may be used to measure the temperature of the user's skin at the location of the wearable device 100. Silicon Labs makes an integrated circuit chip that includes a pulse rate sensor/heart rate sensor as well as blood oximetry (oxygen saturation of the blood). However, while these types of systems may be advantageous in determining whether the system was currently being worn, just the temperature sensor may be employed in accordance with some aspects if a design goal is to preserve battery life. For example, oximetry sensors that employ a light emitting diode and sensor to measure the oxygen saturation and have a high current draw may be omitted.

The biometric sensor module 105 may also be used to detect changes over time in the user's various biomarkers, including heart-related metrics and skin temperature. The changes may be detected through continual and periodic passive objective measurements of the user with the one or more sensors within the biometric sensor module 105.

In accordance with aspects of the invention, the wearable device 100 is embodied in a comfortable wrist band, similar to a watch. However, the device 100 could also work attached to the forearm, worn around the elbow, or attached to essentially any body part. Additionally, the device 100 may be incorporated into an article of clothing such as a glove or other means of holding it on the user. The design of the device 100 in accordance with aspects of the invention is such that it is not obtrusive for an operator to wear, helping to ensure that the operator wears it. Towards that end, the biometric sensor module 105 may be used to detect whether the wearable device 100 is currently being worn (e.g., based on a temperature measurement indicating it is currently against the user's skin). For example, temperature sensors and/or heart rate sensors would work for this purpose. Other biometric sensors of the biometric sensor module 105 may be used for this purpose. The motion sensor 104 and any monitored motions can also be used to determine whether the user is currently wearing the device 100.

The wearable device 100 has a memory 110 which stores a bio-mathematical model for predicting an individual's level of alertness or fatigue. The bio-mathematical model may be a two-process algorithm, which incorporates a sleep-wake homeostasis determination and a circadian rhythm estimation. Sleep-wake homeostasis reflects an individual's need or desire to sleep. The sleep-wake homeostasis determination (or homeostatic sleep drive) may be composed of factors such as time since the user last slept (sleep debt), the length of the last sleeping session of the user, and the quality of the sleep during the last sleeping session of the user. Determining when the user is actually awake or asleep is accomplished using the method referred to as actigraphy. The sleep-wake homeostasis aspect of the model uses accurate actigraphy measures derived from the movements detected by the motion sensor 104, in addition to distal skin, ambient light and heart rate measures, to improve the accuracy of the sleep and wake determinations for the individual. The model also includes a circadian rhythm model aspect of fatigue prediction and estimation which is derived by combining distal skin, heart rate and actigraphy data. This circadian rhythm estimate is able to capture a user's mid-afternoon lull and evening increase in alertness levels.

The memory 110 also stores a generalized default estimation of circadian rhythm which is derived from a sample of a general population of people. The generalized default estimation assumes an approximate 24-hour circadian rhythm cycle. When the individual first puts on the device 100, the device 100 applies the generalized default estimation to the individual. However, over time, the device 100 adjusts the generalized default estimation to reflect the individual's actual circadian rhythm via applying the stored bio-mathematical model, based on various continual and passive measurements of the individual in a closed-loop system. The measurements may include movement, skin temperature, and heart rate. An individual's personal circadian rhythm may actually vary between 23.5 and 25 hours, for example, deviating from the generalized default estimation. Thus, the generalized default estimation is configured to be adjusted according to an estimation of an actual circadian rhythm of the individual, thereby personalizing the predictions of alertness for the individual after applying the bio-mathematical model. For example, an adjustment to the generalized default estimation of the individual could be applied after the individual wears the device 100 for two days, and the measurements over the two days indicate that the generalized default estimation is insufficient to reflect the actual circadian rhythm of the individual.

A processor 108 is coupled to the motion sensor 104 and the biometric sensor module 105. The processor 108 may be a programmable microprocessor. The processor 108 is also coupled to the memory 110 for storing and retrieving data. The processor 108 may execute instructions or apply the bio-mathematical model stored in memory 110 to provide the functionality of the wearable device 100 described herein. The processor 108 may also store data retrieved from the motion sensor 104 and biometric sensor module 105 in memory 110 and retrieve stored data from the memory 110 for processing. The memory 110 may be conventional memory such as, for example, static random access memory (RAM). The processor 108 may be a conventional microprocessor such as a low power consumption embedded processor. A reprogrammable microprocessor device may be employed, which enables firmware upgrades. A suitable processor 108 is an Altera MAX7000A, which operates at 3.3V (an operating voltage range compatible with suitable gyroscopes).

Processor 108 may also be coupled to a clock 112 for monitoring timed and/or scheduled events and a transceiver 114 for transmitting signals to and/or receiving signals from a remote location. The clock 112 may be an integrated circuit clock capable of measuring time (e.g., in fractions of a second such as milliseconds, microseconds, etc.). The transceiver 114 may be, for example, a Bluetooth transmitter, e.g., to enable the wearable device 100 to notify a telematics device, remote computer system, computer application, and/or a smart phone application in the event of a notification. The components of the wearable device 100 may be powered by a battery 116. Battery 116 may be a rechargeable battery such as a lithium ion battery cell.

Processor 108 may monitor the temperature and motion outputs from the motion sensor 104 and the biometric sensor module 105 to determine whether the device is being worn against the skin. The motion outputs from the motion sensor 104 may be used by the processor 108 to monitor the motion of the wearable device 100. The processor 108 may be configured to look for angular motion whose velocity is between 0 dps and 2,000 dps (degrees per second). The low end of the range eliminates small angular shifts due to vibration and the high end of the range eliminates large scale radial motion, such as from a turning truck. The operator's response times as well as recorded temperatures and times may be stored in memory 110 so that, for example, a dispatcher can verify at a later point in time that the device was being properly worn in the event that a telematic system is not available to communicate.

Device 100 additionally may include an ambient light detector 107. The ambient light detector 107 may be used to detect the user's exposure to light. Exposure to light can affect an individual's circadian rhythm and adjust the individual's circadian clock. This may shift the individual's circadian rhythm. The bio-mathematical model can incorporate information acquired by the ambient light detector 107 into a prediction of future changes to an individual's circadian rhythm in response to the individual's light exposure. The ambient light detector 107 may be configured to determine the user's exposure to blue wavelengths of light, which may have an exaggerated effect on the individual's circadian rhythm. The processor 108 may also be coupled to the ambient light detector 107. Processor 108 may monitor and process the outputs measured by the motion sensor 104, the biometric sensor module 105, and the ambient light detector 107.

The processor 108 may also monitor the temperature, heart rate, and motion outputs from the motion sensor 104 and biometric sensor module 105 to assess, using the bio-mathematical model stored in the memory 110, the sleep-wake homeostasis of the individual, including the individual's periods of sleep and wakefulness, by incorporating measurements of motion into actigraphy determinations.

The detection of time sleeping and time since the user last slept can be determined by the processor 108 through analysis of actigraphy movement data indicating the user's lack of movement (which would indicate time during sleep), combined with biomarkers such as heart rate and skin temperature. The processor may adjust and/or confirm the actigraphy determinations using the measurements of the distal skin temperature and the heart rate. For example, the processor 108 could apply measurements of distal skin temperature to the actigraphy determination (with pattern recognition or other techniques) to confirm if an individual is asleep or awake. This could be done with a threshold, looking for a deviation from baseline data, or with a pattern of an increase of skin temperature over a period of time. An increase in distal skin temperature has been shown to correlate with an individual being asleep as well as a decrease in distal skin temperature correlating with the individual being awake.

In addition, the processor 108 may apply measures of ambient light from the ambient light sensor 107 as an additional input to an actigraphical sleep or wakefulness determination, such as in cases where it is not easily determined whether the individual is awake or asleep. For example, if it is not easily determined that the person is asleep or awake, but there is a large amount of ambient light present, the actigraphical output may be a prediction that the individual is awake. On the contrary, an absence of light might indicate that the individual is asleep.

The processor 108 may also apply determinations of body position and heart rate to actigraphy determinations to confirm and/or adjust them. Body position could be used similarly to ambient light in that the body position may provide additional indication as to whether the user is asleep or awake. For example, if the user is standing or sitting they are less likely to be asleep than if they are lying down. Heart rate, similar to skin temperature, has a pattern indicative of whether an individual is sleeping or awake. The processor 108 could use this additional input to better improve the accuracy of the sleep/wake predictions of the actigraphy to improve the sleep-wake homeostasis assessment.

Figure 2:
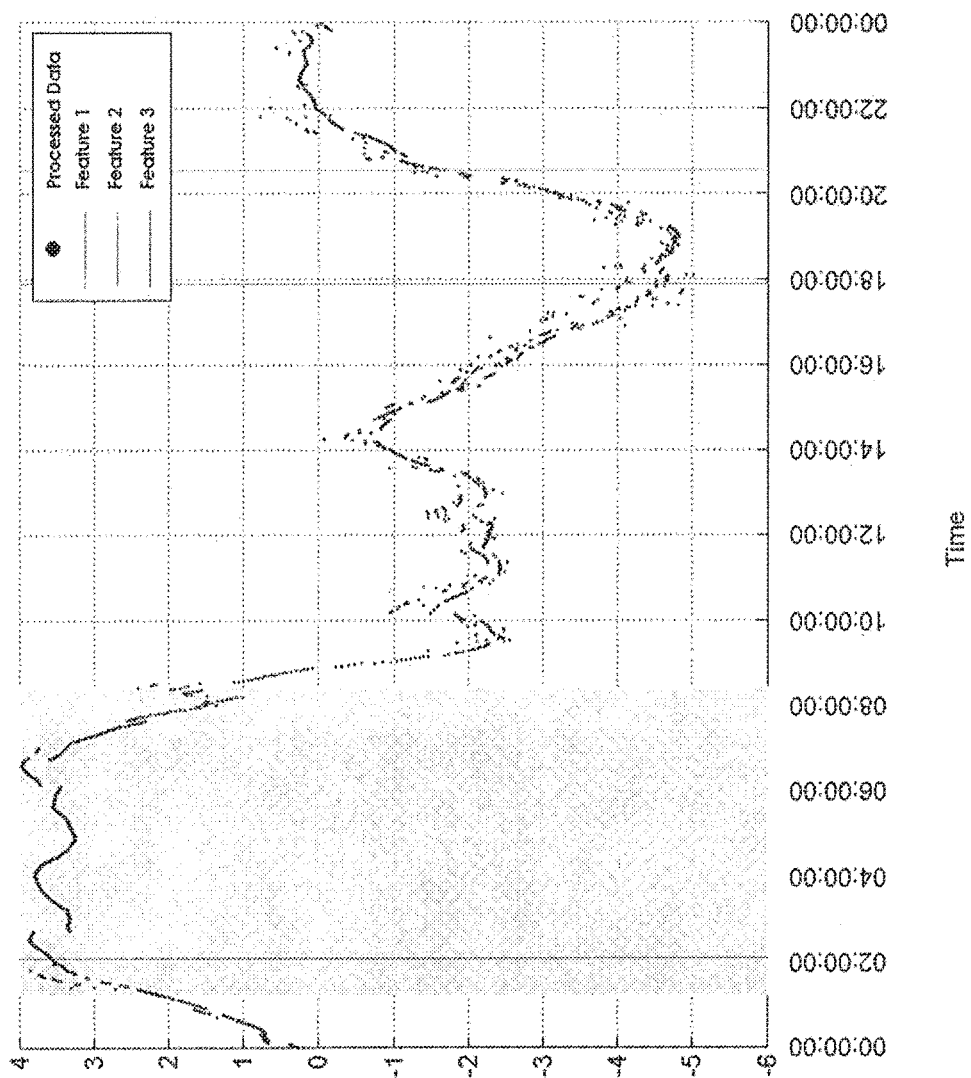
FIG. 2 is a diagram depicting the interaction of sleep-wake homeostasis (the homeostatic sleep drive) with an individual's circadian rhythm in accordance with aspects of the present invention.

The processor 108 also estimates the individual's circadian rhythm. See FIG. 2. The processor 108 may process initial measurements of at least one biomarker, such as skin temperature or heart rate, to estimate the user's personal circadian rhythm. The resulting processed data can be charted, for example, as in FIG. 2, and the processor 108 can identify or extract features or events correlating to specific locations within the individual's circadian rhythm. A user's alertness throughout the day can be strongly correlated with the position of a user within the user's circadian rhythm. The ability to estimate a user's circadian rhythm can provide an accurate prediction of the user's alertness at any point in a given day.

A biomarker for estimating a user's personal circadian rhythm is the user's distal skin temperature. A user's distal skin temperature is correlated with the user's core body temperature. The core body temperature follows the user's circadian rhythm, and the core body temperature will increase during the hours of wakefulness and decrease during typical sleeping hours as a result of following the user's circadian rhythm. The user's levels of alertness will therefore also change with the circadian rhythm. Because the user's body regulates core body temperature by dissipating heat through the limbs of the body, the temperature of the limbs increases when core body heat decreases. Therefore, the measurements of a user's distal skin temperature can be used to accurately estimate the user's personal circadian rhythm by correlating the distal skin temperature with core body temperature, which follows the circadian rhythm of the user. This provides a model of alertness levels for the user.

Distal skin temperature may also be correlated with a user's melatonin levels. A user's level of endogenous melatonin is a reliable and accurate indicator of the user's location within the personal circadian rhythm and therefore an indicator of the user's degree of alertness. Melatonin typically rises during times of decreased alertness (e.g., the period before nightly sleep) and typically falls during times of increased alertness. Skin temperature generally correlates with melatonin levels in that when melatonin levels increase, the skin temperature of the user also increases in connection with the user's circadian rhythm. In this way, skin temperature may act as a correlative proxy for determining the user's current levels of melatonin, and therefore the user's current levels of alertness as determined by the user's location within the personal circadian rhythm.

Initial measurements of a person's distal skin temperature for estimation of a user's personal circadian rhythm and/or melatonin levels may be taken at various locations on the user's body, including feet, arms, wrists, and hands. Other initial measurements of biomarkers that may be incorporated into the processor's 108 estimation of a user's personal circadian rhythm and/or melatonin level may include, but are not limited to, heart-related metrics such as heart rate.

An example of estimating a user's personal circadian rhythm may begin with the user wearing the wearable apparatus 100 at a distal location on the body, such as the wrist, for a testing period. The testing period may have a duration of two or more days. Ambulatory skin temperatures may be measured by the temperature sensor 105a at a frequency of once per minute for the span of the at least two days. Based on the data derived from the distal skin temperature measurements, the processor 108 may estimate a user's personal circadian rhythm. Other initial measurements of biomarkers over the testing period may also be used to estimate the circadian rhythm of a user.

The circadian rhythm estimation by the processor 108 is enabled by gathering measurements of an individual's distal skin temperature and/or their heart rate for a period of time. The processor 108 generates data points derived from measurements of distal skin temperature and heart rate. The processor 108 may also incorporate measurements of movements by the individual to refine the data points. The data points represent points of time within the individual's actual circadian rhythm, and the processor 108 can use these data points to estimate the individual's overall circadian rhythm by compiling them over time as a progression. The processor 108 also uses these data points to adjust the generalized default estimation stored in the memory 110 to better reflect the individual's actual circadian rhythm. The processor 108 may apply pattern recognition and/or machine learning techniques to effect the adjustment such that the circadian rhythm determination is personalized to the individual.

An individual's circadian rhythm typically does not change drastically from day to day. However, an individual's activities may change each day. These activities can "mask" the indicators of an individual's circadian rhythm, which is typically stable. Because the distal skin temperature and/or heart rate are affected by other outside "masking" events (such as walking, sleeping, etc.), the processor 108 may have to apply additional signal processing techniques to separate, or "demask," the skin temperature or heart rate data from these "masking" non-circadian rhythm events. The processor 108 applies a "demasking" algorithm to remove the "masking events" from the underlying skin temperature and heart rate data (i.e., raw circadian data) to provide an accurate prediction of circadian rhythm. For example, the masking event of a person periodically getting up and walking (for example, from one office to another) does not happen at the exact same time every day. This means that data points gathered at the same time point each day (for example, at 12:05 pm every day) can be examined across multiple days with signal processing techniques employed which can remove the outlying "masking" factors and retain the underlying consistent signal. This is most easily implemented with a technique of averaging each of multiple points in a given 24 hour period across multiple days; however, additional signal processing techniques such as filtering may be used. Similarly, this same principal may be applied to heart rate measures which are similarly affected by circadian rhythm but have historically not been usable because of masking effects.

Variables considered in "demasking" of distal skin measurements and heart rate measurements include body position and activity of the individual, which are "masking events" that may distort the underlying circadian rhythm signals from skin temperature and heart rate. For example, the typical environment in which a circadian rhythm signal is observed is in a laboratory setting where the user lays in a bed in a fixed position, with minimal food intake and no movement. "Demasking" is the process of removing the effects of events occurring outside such a controlled environment. As an example, the individual may engage in jogging. When this occurs, the individual's distal skin temperature is reduced as the individual begins to sweat. Additionally, the individual's heart rate increases due to physical activity. Because of this, the underlying circadian signal is typically lost. However, the processor 108 applies a "demasking" algorithm which is able to preserve the underlying circadian signal in the presence of these masking effects by incorporating historical information saved in the memory for a specific time period and the situational information, if the device 100 and the processor 108 know that the individual is running, the processor 108 can determine that the data being received is bad data and can be discarded, or its significance can be reduced in determining actual alertness via the bio-mathematical model.

In a preferred embodiment the circadian rhythm estimation is also improved by a concept of a quality factor that is associated with each data point. If additional information can be known about the condition in which a data was captured (for example if the user was walking or asleep) then this data point can be given a quality factor. For example, if a user is walking when a data point is captured then it would be considered a low quality data point, conversely if a user has been sitting for a period of time when a data point is captured, it would be considered a high quality data point. Using this concept of a quality factor, the accuracy of the circadian rhythm can be improved as all data points are not treated as equal. The processor 108 may "demask" or apply a quality factor to skin temperature or heart rate data within a data point by averaging a given data point for a specific time period over several days. For example, if the distal skin temperature is gathered at exactly 12:05 PM on a given day, an individual may be running to catch the bus, resulting in the data point being given a low quality factor. The next day an additional data point would be gathered at 12:05 PM. This time the user is sitting in a chair and so this data point would be a high quality data point. By applying a weighted average to these data points a more accurate "demasked" distal skin temperature or heart rate can be obtained by the processor 108.

The processor 108 uses the quality factor as a coefficient for a weighted average for combining several days' worth of circadian rhythm data for a given point in the day. For example, the processor 108 may take a data point at 12:05 pm on Tuesday and 12:05 pm on Wednesday. Tuesday was assessed a quality factor of 0.1, while Wednesday had a quality factor of 0.9. The resulting weighted average would be calculated by the processor as (0.1*Tuesday_data+ 0.9*Wednesday_data). This provides a better estimate than simply averaging the data across several days, because the processor 108 is not treating all data points as equal value.

Additionally, the processor 108 can estimate the actual time period of the circadian rhythm (which, for a typical individual, is not exactly 24 hours) by incorporating the trends in the skin temperature and/or heart rate. With the skin temperature and/or heart rate data allocated a quality factor and/or "demasked," the processor 108 can then normalize the data and assume the circadian rhythm is a phase shifted and correlated pattern. Additionally, the melatonin levels can be predicted by sharp increases in the normalized distal skin temperature data, which can be used as a marker for circadian rhythm coefficient (the phase $\Phi$) shift and period ($\tau$) of an individual's circadian rhythm.

Figure 3:
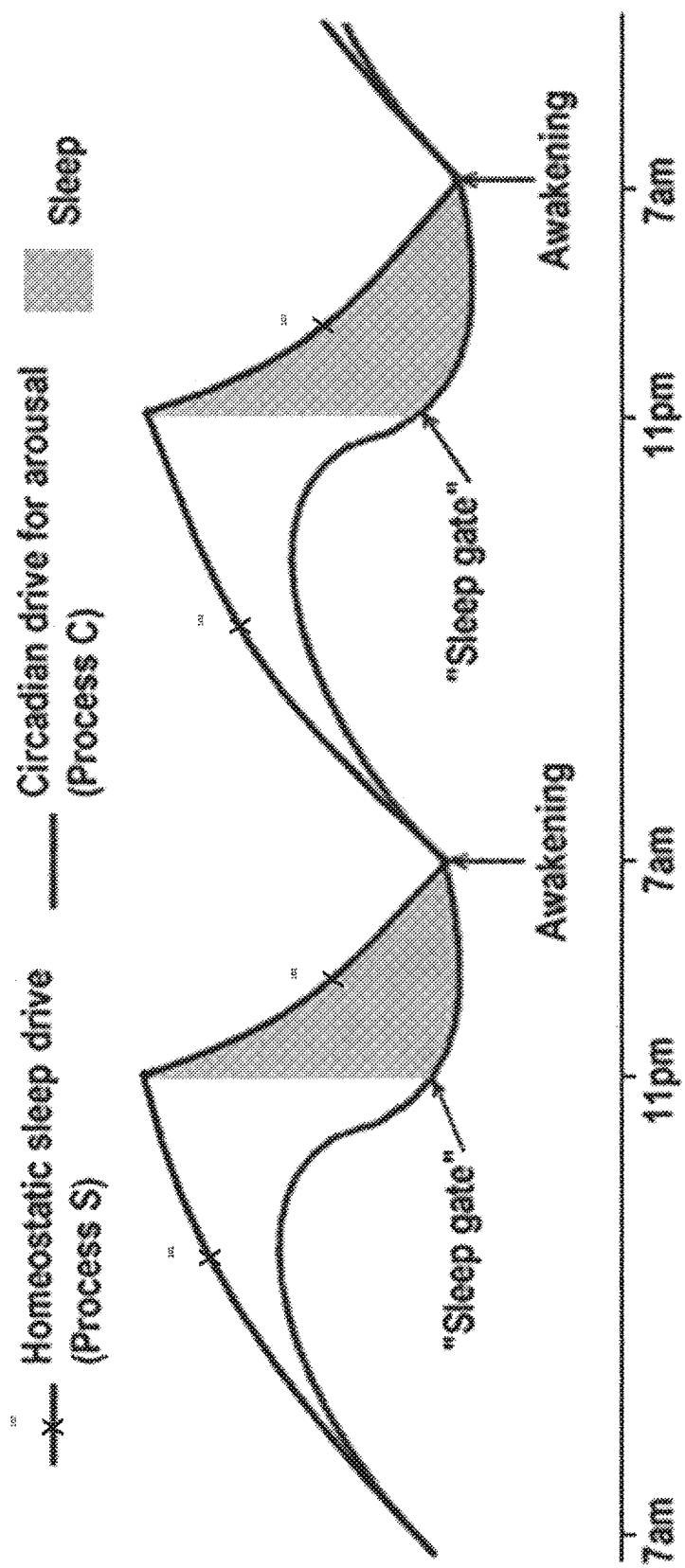
FIG. 3 is a chart depicting exemplary events or features within an individual's circadian rhythm, in accordance with aspects of the present invention.

The processor 108 can also combine the sleep-wake homeostasis determinations with the actual circadian rhythm estimation according to the bio-mathematical model to result in a prediction of alertness of the individual. This results in a more accurate and personalized alertness prediction for the individual. Sleep-wake homeostasis and circadian rhythm work together within the individual to result in the individual's ever-changing alertness. See FIG. 3. The circadian rhythm can then be combined with the sleep homeostasis information by the bio-mathematical model to create an overall estimate of alertness. Each input to the bio-mathematical model may be combined using pattern recognition and/or machine learning techniques. Some of these techniques include weighting one portion over another. The weighted portions of the bio-mathematical model may be statically or dynamically defined. For example, the weight given to the circadian rhythm is based upon the estimated quality of the data the processor 108 has gathered.

Figure 4:
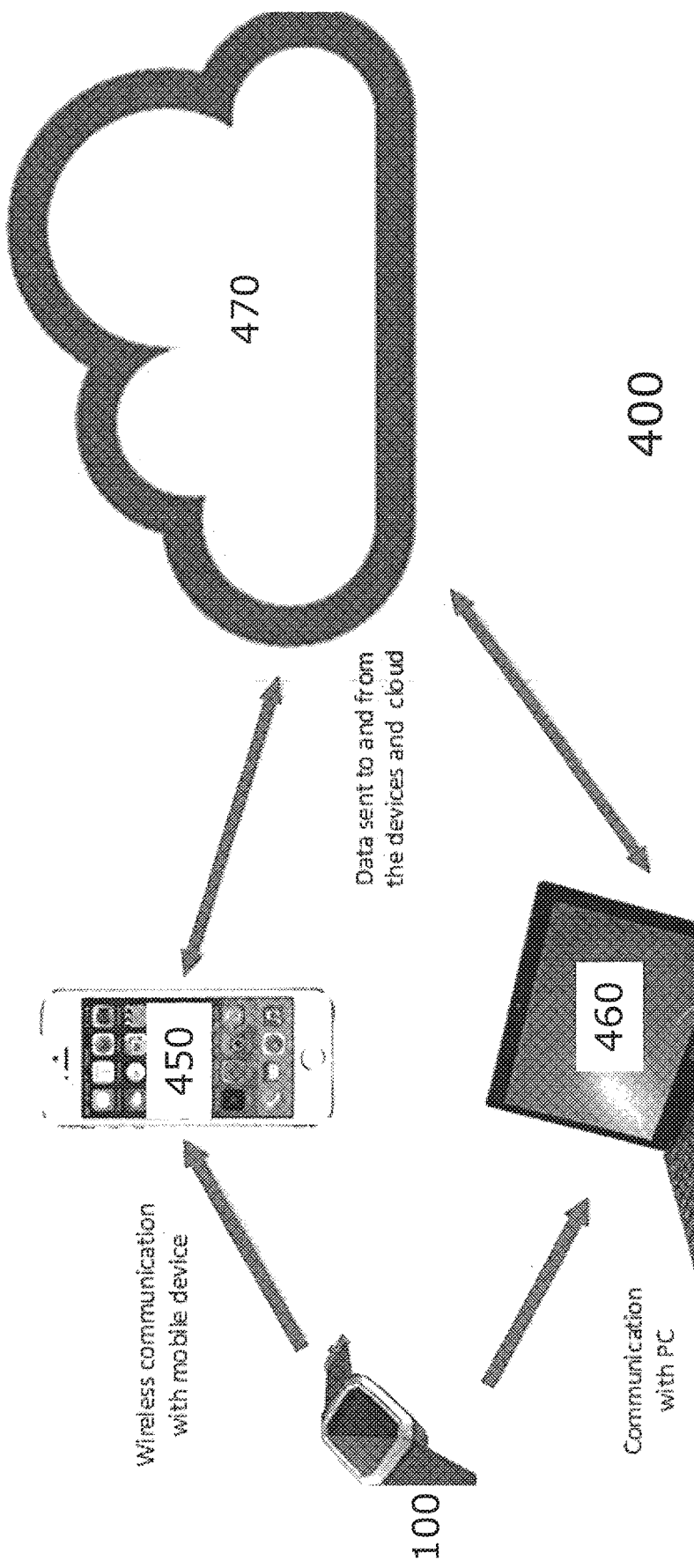
FIG. 4 is a block diagram of a system including a wearable device as described herein in communication with external devices in accordance with aspects of the invention.

FIG. 4 depicts a system 400 including a wearable device 100 in accordance with aspects of the invention. The wearable device 100 may be in communication with, for example, a smart device 450 and/or an external computing device 460. The smart device 450 may be a mobile device such as a smart phone. The external computing device 460 may be a personal computer or the like. Data collected by the wearable device 100 may be communicated to a smart device 450 and/or an external computing device 460. The smart device 450 and/or the external computing device 460 may also communicate other information to the wearable device 100.

The smart device 450 and/or the external computing device 460 may have applications or other software modules that can display, store, and/or further process the data received from the wearable device 100. For example, the smart device 450 may have a software application that displays charts of an individual's alertness predictions or fatigue scores over time, derived from data received from the wearable device 100 and stored by the smart device 450. The smart device 450 and/or the computing device 460 can also be used to alert an individual if the data received from the wearable device 100 predicts fatigue for the individual. Additionally, the smart device 450 and/or the computing device 460 can communicate and exchange data with a data cloud 470. Thus, data received by the smart device 450 and/or the computing device 460 can be transferred for storage to the cloud 470, and the smart device 450 and/or the computing device 460 can, for example, retrieve the data stored in the cloud 470 to generate charts or diagrams of an individual's fatigue-related data over time. In addition, a third party, such as a manager or dispatcher, may be able to view information regarding the individual's fatigue or alertness via the smart device 450 and/or the computing device 460.

Figure 5:
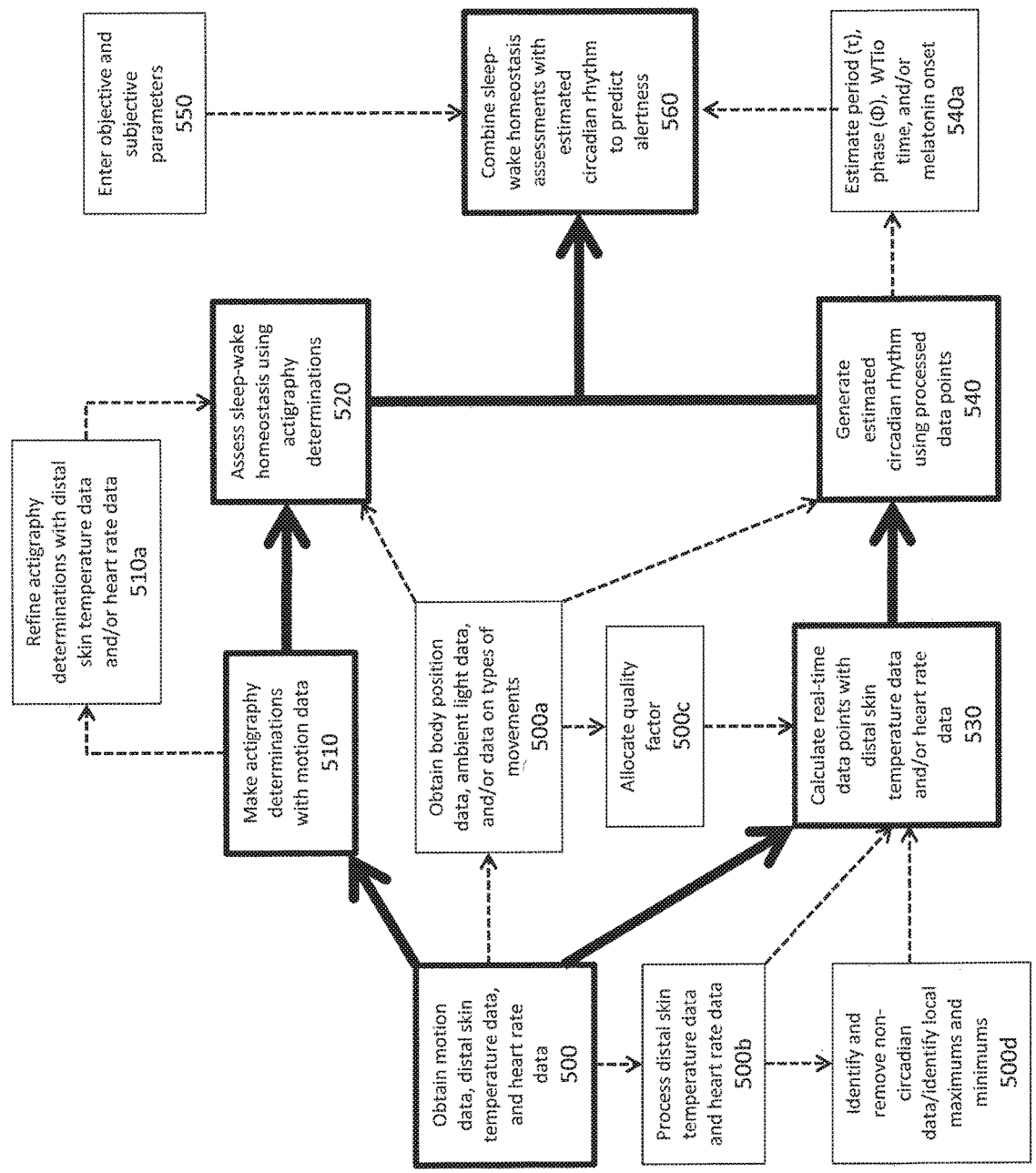
FIG. 5 is a flow chart of steps for predicting the alertness of a user in accordance with aspects of the invention.

FIG. 5 depicts steps for predicting alertness of an individual in accordance with aspects of the invention. First, at step 500, motion data produced by a motion sensor, distal skin temperature data produced by a temperature sensor, and/or heart rate data produced by a heart rate monitor may be obtained or received by a processor 108. Each of the motion sensor, the temperature sensor, and the heart rate monitor may be associated with a wearable device 100 worn by the individual. The motion sensor may also produce data on the individual's body position or data on the types of movements performed by the individual at step 500*a*, which may also be obtained by the processor 108. Step 500*a* may also include ambient light data produced by an ambient light sensor being obtained or received by the processor 108.

At step 500*b*, the processor may process the distal skin temperature data and/or the heart rate data to refine the data as directed by a bio-mathematical model, which may be stored in a memory of the wearable device 100. The processor 108 may apply signal processing techniques, including, for example, low-pass filtering and moving averages, to effect the processing of the skin temperature data and heart rate data. Such processing/filtering removes "noise" from the distal skin temperature data signal and/or the heart rate data signal to produce a cleaner, more accurate signal.

At step 500*c*, the processor may allocate a quality factor to the skin temperature data and/or the heart rate data based on at least one of the data on the individual's body position and the types of movements performed by the individual in accordance with the bio-mathematical model.

At step 500*d*, the processor may identify circadian and non-circadian data within the skin temperature data and/or the heart rate data (i.e., raw circadian data), and remove the non-circadian data to obtain refined circadian data (i.e., "demasking" the circadian data). Circadian data is defined as data derived from circadian rhythm events, while non-circadian data is data derived from non-circadian events. The processor may remove the non-circadian data using pattern recognition and/or machine learning techniques. The processor 108 may also detect local maximum events and local minimum events within the refined/demasked circadian data to identify potential times of fatigue risk for the individual.

At step 510, the processor 108 may make actigraphy determinations using the motion data it received from the motion sensor. The processor 108 may then refine the actigraphy determinations at step 510*a* using at least one of the distal skin temperature or the heart rate data to make more accurate actigraphy determinations.

The processor 108 may then use the actigraphy determinations at step 520 to assess the individual's sleep-wake homeostasis bio-mathematical model, including periods of sleep and wakefulness of the individual. This assessment may occur repeatedly. The processor may use either the raw actigraphy determinations or the refined actigraphy determinations to assess the individual's sleep-wake homeostasis. Additionally, the processor 108 may incorporate data on the individual's body position to refine the sleep-wake homeostasis assessments. The processor may also refine the sleep-wake homeostasis assessments of the individual by incorporating the ambient light data.

At step 530, the processor 108 may calculate data points using at least one of skin temperature data or the heart rate data. The processor 108 may incorporate the processed of skin temperature and/or the heart rate data from step 500*b*, or unprocessed data to calculate the data points. Additionally, the processor 108 may incorporate the quality factor allocated to the skin temperature data and/or the heart rate data from step 500*c* into the calculation of the data points. The processor 108 may also incorporate the skin temperature data and/or the heart rate data with or without the non-circadian data removed to calculate the data points.

At step 540, the processor 108 may generate an estimated circadian rhythm for the individual. This may occur periodically. The processor 108 may generate the estimated circadian rhythm by using the processed data points to refine a default circadian rhythm stored in the memory of the wearable device. The default circadian rhythm may be derived from a sample of a general population of people, and the default circadian rhythm may assume an approximate 24-hour circadian rhythm cycle. Additionally, the processor 108 may refine the estimated circadian rhythm by incorporating the ambient light data.

The processor 108 may also estimate the individual's circadian rhythm coefficient (current phase $\Phi$), the individual's wake/sleep coefficient, the individual's circadian rhythm period ($\tau$), the individual's sleep onset time, and/or the individual's melatonin onset at step 540*a*. Each individual may have a different circadian rhythm coefficient/phase ($\Phi$) shift, which means each individual's circadian rhythm period ($\tau$) may start at different times. The sleep onset time can be determined by, for example, identifying low points within demasked distal skin temperature of an individual, followed by an increase (for example, a 35% increase) in the demasked distal skin temperature. Low points correlate with high levels of alertness within the individual, while a 35% increase from a low point indicates melatonin onset. Melatonin onset can be used, in turn, as a marker for the time at which an individual's circadian rhythm cycle or period ($\tau$) begins.

At step 550, the individual may enter objective and subjective parameters into the device 100. The individual may also enter the subjective and objective parameters on a smart device 450 and/or an external computing device 460, such that the parameters may be communicated to and used by the wearable device 100. Parameters that may be entered include, but are not limited to, prescribed motions as described in detail by U.S. Utility application Ser. No. 14/848,771, data regarding the individual's medical history, susceptibility to the effects of not getting enough sleep, data from questionnaires answered by the individual, and subjective assessments by the individual of his or her own levels of alertness.

At step 560, the processor 108 may combine the sleep-wake homeostasis assessments with the estimated circadian rhythm with the bio-mathematical model to predict an individual's level of alertness or to generate a fatigue prediction. The processor 108 may incorporate the subjective and objective parameters to further refine fatigue predictions for the individual. These parameters may be weighted in a non-linear manner using pattern recognition or machine learning techniques to incorporate them into the refinement of the prediction in accordance with a bio-mathematical model. The processor 108 may also use the estimated circadian rhythm coefficient/phase ($\Phi$), circadian rhythm period ($\tau$), wake/sleep coefficient, sleep onset time, and/or melatonin onset to predict the individual's alertness. The processor 108 may also incorporate either refined or unrefined sleep-wake homeostasis assessments and/or a refined or unrefined estimated circadian rhythm when making the prediction according to a bio-mathematical model. The processor 108 may also refine the prediction of alertness for the individual by using the detected local maximum events and the local minimum events. The prediction of alertness may thereafter be communicated by the wearable device 100 to an external computing device 460 and/or a smart device 450 for display, storage, and/or further processing.

Figure 6:
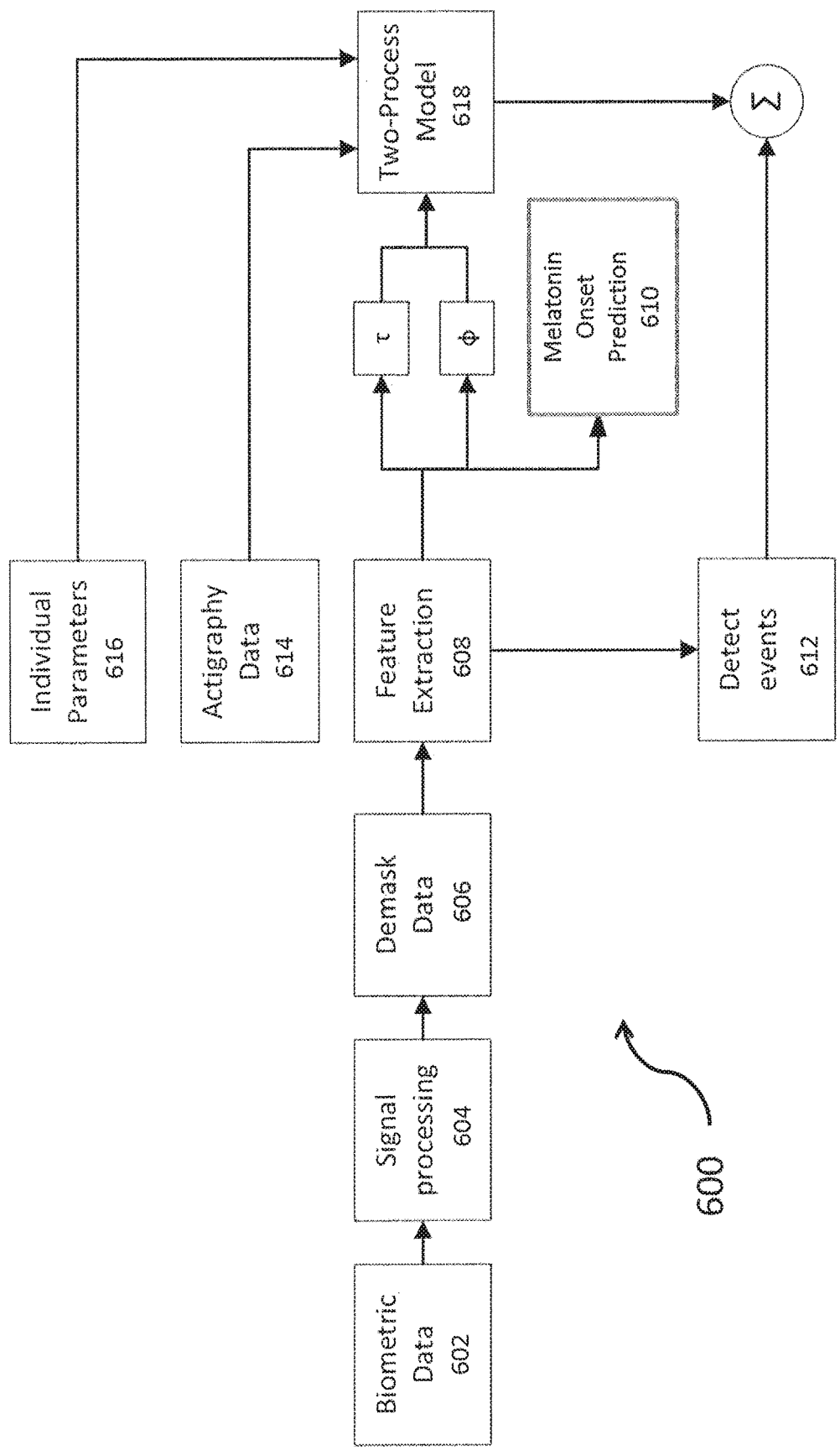
FIG. 6 is a flow chart of an exemplary method for implementing concepts according to FIG. 5 in accordance with aspects of the invention.

FIG. 6 depicts steps of an exemplary method 600 for implementing the concepts according to FIG. 5. First, at step 602, data on an individual's movements, distal skin temperature, and heart rate may be obtained. A wearable device 100, or a processor 108 of the wearable device may obtain this data as signals from a motion sensor 104, a temperature sensor 105a, and/or a heart rate monitor 105b. The wearable device 100 or the processor 108 may also receive signals from the motion sensor 104 indicating the individual's body position.

At step 604, signals received from the temperature sensor 105a and the heart rate monitor 105b may be processed by the processor 108 to clean up the data as directed by the bio-mathematical model, which is, for this exemplary method 600, a two-process algorithm. The processor 108 may apply low-pass filtering and moving averages to improve the signal processing of the skin temperature and heart rate data.

At step 606, the skin temperature and heart rate data may be "demasked" in accordance with the two-process algorithm so as to remove obscuring signals caused by non-circadian events from the underlying measured data signals of distal skin temperature and heart rate of the individual. These events include, but are not limited to, sleep, physical activities, and certain body positions. The underlying signals related to circadian rhythm may be "demasked," for example, by averaging several days' worth of data together. The "demasked" data, including skin temperature heart rate data can then be used to generate data points for the individual's actual circadian rhythm. A quality factor may also be allocated at step 606 to skin temperature and/or heart rate data based on the type of detected movements made by the individual.

At step 608, the feature extraction aspect of the two-process algorithm is employed to extract meaningful events or circadian rhythm-related features from the measured and "demasked" signals. These meaningful events or features may include slow increases in distal skin temperature which follow the individual's circadian rhythm and indicate decreasing levels of alertness. Also, sudden increases in distal temperature may indicate sudden changes in alertness levels. Machine learning and/or pattern recognition techniques can be used to extract the events and/or patterns. Several commonly used functions may be employed by the algorithm to perform the feature extraction, including peak detection algorithms, interpolation between points, and the cosinor function.

At step 610, sleep onset time may be determined from the "demasked" data, which then may be used to estimate the current phase/circadian rhythm coefficient ($\Phi$) or location the individual is in within the individual's circadian rhythm period ($\tau$). Each individual may have a different phase ($\Phi$) shift, which means each individual's circadian rhythm period ($\tau$) may start at different times. The sleep onset time can be determined by identifying low points within the circadian rhythm, followed by a, for example, 35% increase in the circadian rhythm. Low points correlate with high levels of alertness within the individual, while a 35% increase from a low point indicates melatonin onset. Melatonin onset can be used, in turn, as a marker for the time at which an individual's circadian rhythm cycle or period ($\tau$) begins.

At step 612, local maximum and minimum points or events within "demasked" skin temperature data and/or heart rate data can be detected and identified as potential times of fatigue risk for a given individual. These detected events may correlate with increased levels of drowsiness. For example, an increase in skin temperature around the 2:00 pm-4:00 pm timeframe may be identified as a decrease in alertness, something that is often observed in the mid-afternoon hours.

At step 614, actigraphy data from the individual can be used to determine the individual's sleep and wakefulness periods, and the individual's resulting sleep-wake homeostasis for the two-process algorithmic model. This can be determined solely using the detected movements made by the individual. However, other measurements, such as heart rate, distal skin temperature, and ambient light exposure can be incorporated to make the determination of the individual's sleep and activity periods more accurate.

At step 616, the individual can input other subjective and objective parameters into the device 100. The individual may also enter the subjective and objective parameters on a smart device 450 and/or an external computing device 460, such that the parameters may be communicated to and used by the wearable device 100. These parameters can be used to further refine predictions of alertness within the individual. Parameters that may be input include, but are not limited to, prescribed motions as described in detail by U.S. Utility application Ser. No. 14/848,771, data regarding the individual's medical history, susceptibility to the effects of not getting enough sleep, data from questionnaires answered by the individual, and subjective assessments by the individual of his or her own levels of alertness. These parameters may be weighted in a non-linear manner using pattern recognition or machine learning techniques to incorporate them into a refinement of the two-process algorithmic model.

At step 618, the inputs from the circadian rhythm aspect, including the period ($\tau$), phase/circadian rhythm coefficient ($\Phi$), event features, and melatonin onset derived from the data points are combined with the input of the sleep-wake homeostasis aspect of the two-process algorithm to produce a performance metric that predicts the alertness levels of the individual. Each of these inputs to the algorithm is combined using pattern recognition techniques and/or machine learning techniques. Some of these techniques may include weighting one portion of the algorithm over another. For example, the weight allocated to the circadian rhythm aspect of the algorithmic model is based upon the estimated quality of the data gathered. This alertness level prediction can be further refined using the inputs derived from step 616, the other objective and subjective parameters. These objective and subjective parameters may also be weighted prior to incorporation into the prediction of the individual's alertness.

Figure 7:
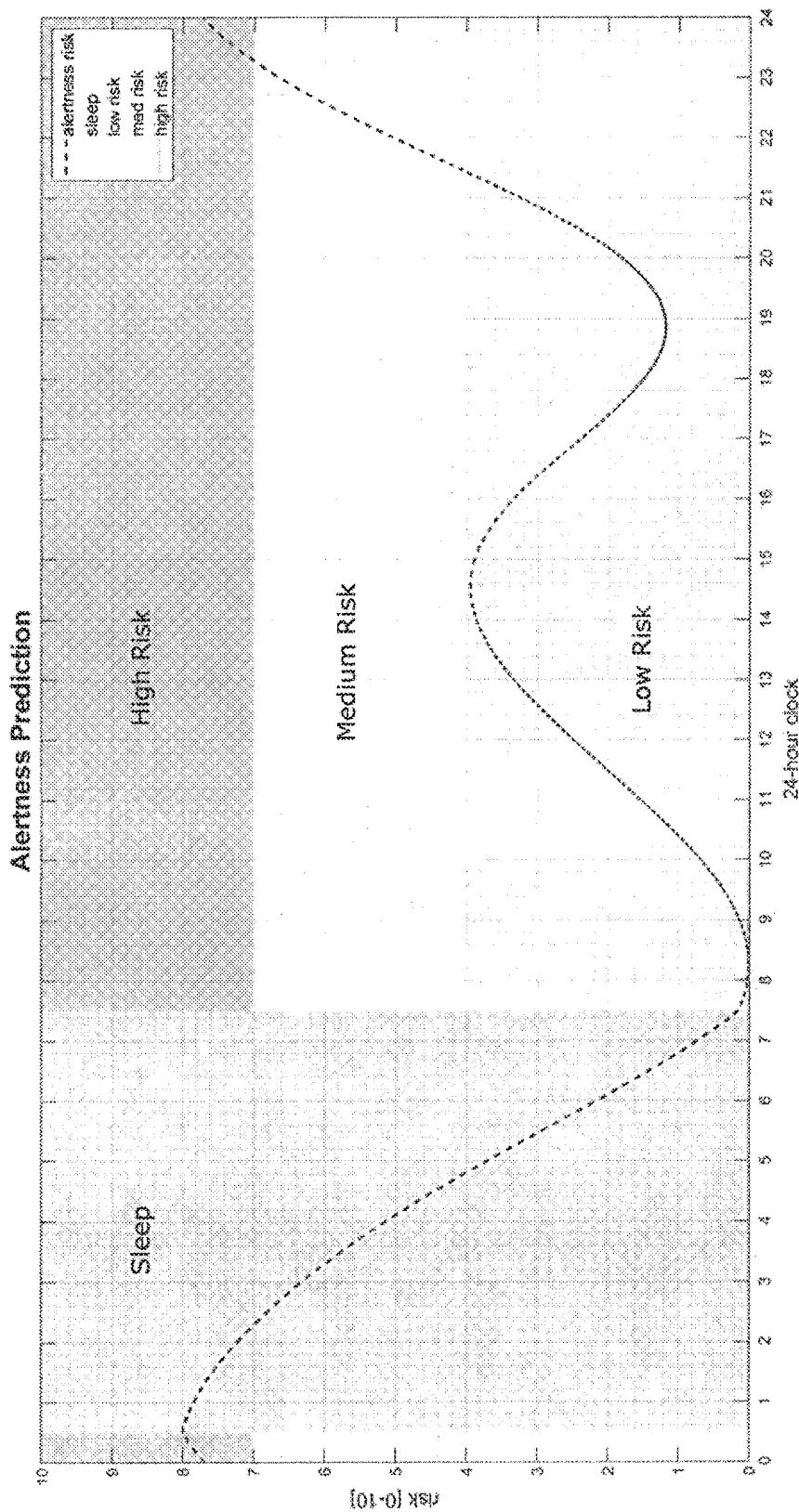
FIG. 7 is a diagram of an alertness prediction output from a bio-mathematical model in accordance with aspects of the invention.

FIG. 7 depicts an alertness prediction output for an individual over a 24-hour period, derived from the bio-mathematical model. The broken line represents the individual's alertness risk on a scale from 0 to 10, wherein 10 represents the highest fatigue risk and serves as the fatigue risk baseline. The diagram displays the individual's alertness prediction changing over time throughout the 24-hour period. The diagram also displays a period of sleep for the individual and depicts alertness predictions for the individual that indicate a low, medium, and high fatigue risk.

Figure 8:
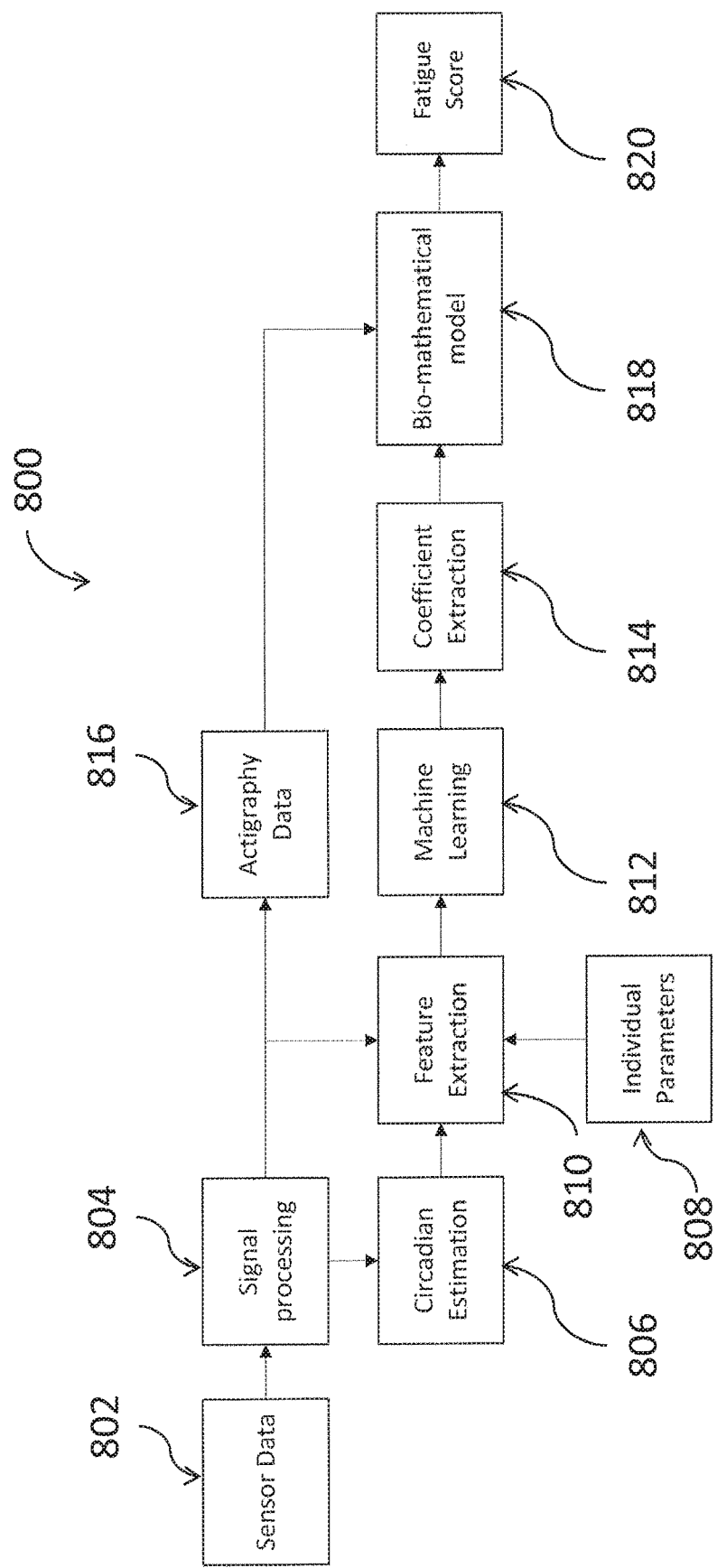
FIG. 8 is a flow chart of an exemplary method for estimating fatigue in accordance with aspects of the invention.

FIG. 8 depicts steps of a method 800 for estimating fatigue of a wearer/individual in accordance with aspects of the invention. One or more of the steps of method 800 may be omitted and/or repeated and/or performed in order (including simultaneously) that may vary from those disclosed herein without deviating from the scope and spirit of the present invention.

At step 802, sensor data is obtained. The sensor data may include information about the wearer, for example, movements, position, distal skin temperature, and/or heart rate. Additionally, the sensor data may include environmental conditions, for example, ambient light levels and/or temperature. A wearable device 100, or a processor 108 of the wearable device, may obtain the sensor data as signals from, for example, a motion sensor 104, a temperature sensor 105a, a heart rate monitor 105b, and/or a light sensor.

At step 804, signal processing is performed. For example, signals received from the temperature sensor 105a and the heart rate monitor 105b may be processed by the processor 108 to clean up the data as directed by the bio-mathematical models described herein. The processor 108 may, for example, apply low-pass filtering and moving averages to improve the quality of the signal for the skin temperature and heart rate data.

At step 806, circadian rhythm is estimated from the received and processed signals. The processor 108 may identify circadian and non-circadian data within the skin temperature data and/or the heart rate data (i.e., raw circadian data), and remove the non-circadian data to obtain refined circadian data (i.e., "demasking" the circadian data). The processor 108 may remove the non-circadian data using pattern recognition and/or machine learning techniques.

At step 808, individual parameters are obtained. The individual parameters may include subjective and/or objective parameters. Individual parameters may include, but are not limited to, data regarding the individual's medical history, susceptibility to the effects of not getting enough sleep, ability to perform prescribed motions, data from questionnaires answered by the individual, and subjective assessments by the individual of his or her own levels of alertness. The individual parameters can be received from the wearer via, for example, a user input of the device 100 or a smart device 450 and/or external computing device 460, such that the parameters may be communicated to and used by the wearable device 100. These parameters can be used to further refine predictions of alertness for the individual.

At step 810, features are extracted from the received and processed signals, the estimated circadian rhythm, and the obtained individual parameters. The extracted features may include markers indicating the shape of the circadian rhythm, such as local circadian highs and lows (e.g., the "post-lunch dip"); information regarding the user's sleep habits both on working days and free days, such as sleep latency, sleep inertia, circadian lows, circadian preference (morning vs. evening person), habitual sleep opportunity and location (phase), average sleep time, and napping habits; general medical information, such as age, sex, BMI, etc. In one embodiment, the extracted features are (1.) on a work day: wake time, alarm use, energy dip time, bed time, mid-sleep time, sleep duration, sleep latency; (2.) on a free day: wake time, energy dip time, bed time, mid-sleep time, sleep duration, sleep latency; (3.) age; (4.) sex; (5.) BMI; and/or (6.) corrected mid-sleep phase information. The features may be extracted by simple averaging, peak and valley detection (in a signal) before and after transforming the data (via derivative, integral, phase shift, etc.), algebraic combinations, transformation based on a mapping function, transformation of data into frequency domain, etc.

At step 812, one or more pattern recognition and/or machine learning algorithms are applied to the extracted features to identify how the extracted features can be used to determine coefficients. The processor 108 may apply pattern recognition and/or machine learning techniques to personalize circadian rhythm factors to the individual and/or to weight one factor over another. The weighted portions of the algorithmic model may be statically or dynamically defined. The pattern recognition and/or machine learning algorithms may apply peak detection algorithms, interpolation between points, and/or the cosinor function, in one embodiment, a regression-based machine learning algorithm is applied to the extracted features to determine the coefficients to be extracted in the next step.

At step 814, coefficients are extracted, e.g., by processor 108. In one embodiment, four coefficients are extracted. The four coefficients may include a circadian rhythm coefficient (phase $\Phi$), a wake/sleep coefficient, a circadian rhythm weighting coefficient, and a wake/sleep weighting coefficient. The processor 108 may extract the coefficients by transforming the output (applying a mapping, phase shift, etc.) of the machine learning of step 812 so that it can be fed into the bio-mathematical model of step 818 described below.

At step 816, actigraphy data is determined. The processor 108 may make actigraphy determinations using the processed motion data received from the motion sensor. The processor 108 may then refine the actigraphy determinations using at least one of distal skin temperature and/or heart rate data to make more accurate actigraphy determinations, e.g., is the person awake or asleep, is the person seated or moving, etc.

At step 818, a bio-mathematical model is applied, e.g., by processor 108, to the extracted coefficients and determined actigraphy data. In one embodiment, the bio-mathematical model includes at least two sub-models, e.g., an awake sub-model that is applied when an individual is awake and an asleep sub-model that is applied when an individual is asleep. Whether the individual is awake or asleep may be determined by the processor 108 based on the actigraphy data, and the appropriate model is applied based on the determined awake/asleep condition.

At step 820, a fatigue score is generated. The fatigue score may be generated by processor 108. The fatigue score, or an indication thereof, may be presented to the user or a person of interest (e.g., an employer). If the fatigue score indicates a high level of fatigue, stimulus may be presented to the user (e.g., a vibration by the wearable device).

Figure 9A:
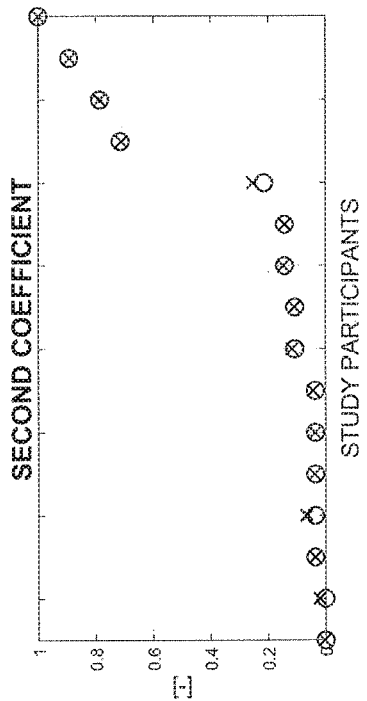
FIG. 9A is a graph of a first coefficient that may be extracted in the method of FIG. 8.

FIG. 9A depicts first coefficient values for 16 individuals. The depicted first coefficient values are circadian cycle/phase ($\Phi$) values. The optimal value for a coefficient is represented by a "o" and the extracted value determined by the coefficient extractor for the circadian cycle is represented by an "x".

Figure 9B:
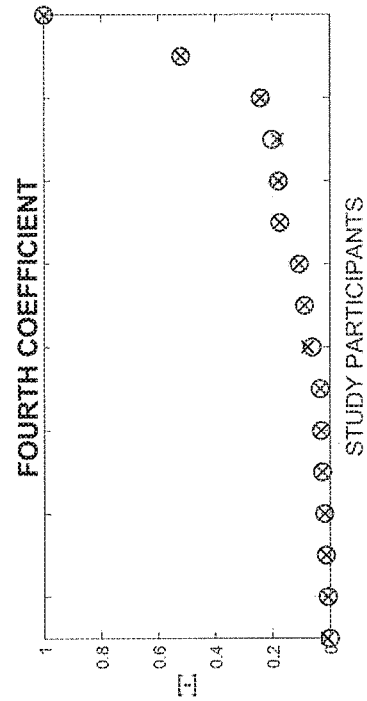
FIG. 9B is a graph of a second coefficient that may be extracted in the method of FIG. 8.

FIG. 9B depicts second coefficient values for 16 individuals. The depicted second coefficient values are wake/sleep cycle values. The optimal value for a coefficient is represented by a "o" and the extracted value determined by the coefficient extractor for the wake/sleep cycle is represented by an "x".

Figure 9C:
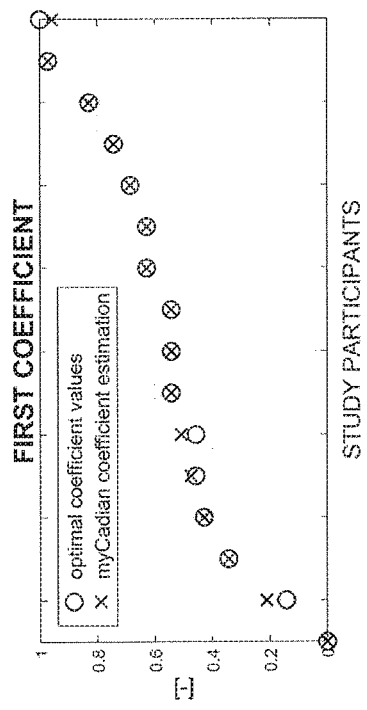
FIG. 9C is a graph of a third coefficient that may be extracted in the method of FIG. 8.

FIG. 9C depicts third coefficient values for 16 individuals. The depicted third coefficient values are circadian cycle weighting values. The optimal value for a coefficient is represented by a "o" and the extracted value determined by the coefficient extractor for the circadian cycle weight is represented by an "x".

Figure 9D:
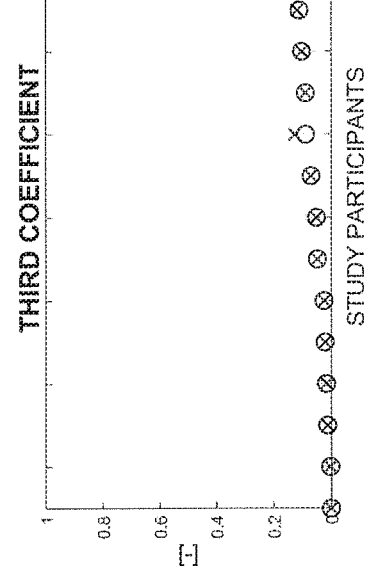
FIG. 9D is a graph of a fourth coefficient that may be extracted in the method of FIG. 8.

FIG. 9D depicts fourth coefficient values for 16 individuals. The depicted fourth coefficient values are wake/sleep cycle weighting values. The optimal value for a coefficient is represented by a "o" and the extracted value determined by the coefficient extractor for the wake/sleep cycle weight is represented by an "x".

The information depicted in FIGS. 9A-9D illustrate the features extracted using techniques in accordance with aspects of the invention are accurate at the individual level—enabling accurate prediction of an individual's fatigue.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A device for monitoring and predicting alertness of an individual, the device comprising:
   one or more sensors configured to obtain information signals about the individual, the sensors comprising at least one of:
      a motion sensor configured to produce movement data or body position data of the individual,
      a temperature sensor configured to produce distal skin temperature data of the individual, and
      a heart rate monitor configured to produce heart rate data of the individual;
   a memory configured to store:
      a default circadian rhythm configured to be refined with data derived from the information signals about the individual to generate an estimated circadian rhythm for the individual, and
      a bio-mathematical model configured to generate a fatigue score for the individual;
   a processor coupled to the one or more sensors and to the memory, configured to:
      receive the information signals about the individual,
      estimate a circadian rhythm of the individual by incorporating the information signals about the individual to refine the default circadian rhythm,
      extract features from the information signals about the individual and the estimated circadian rhythm,
      extract at least one coefficient from the extracted features using at least one pattern recognition algorithm or machine learning algorithm,
      apply the bio-mathematical model to the at least one extracted coefficient, and
      generate the fatigue score for the individual from the at least one extracted coefficient using the bio-mathematical model.

* * * * *